US012062486B2

(12) United States Patent
Hughes et al.

(10) Patent No.: US 12,062,486 B2
(45) Date of Patent: Aug. 13, 2024

(54) MODULAR MAGNETIC FIELD COMPENSATION COIL ARRAY

(71) Applicant: FieldLine Inc., Boulder, CO (US)

(72) Inventors: Kenneth J. Hughes, Lafayette, CO (US); Svenja Knappe, Boulder, CO (US); Tyler L. Maydew, Broomfield, CO (US); Orang Alem, Erie, CO (US)

(73) Assignee: FieldLine Inc., Boulder, CO (US)

( * ) Notice: Subject to any disclaimer, the term of this patent is extended or adjusted under 35 U.S.C. 154(b) by 99 days.

(21) Appl. No.: 17/836,438

(22) Filed: Jun. 9, 2022

(65) Prior Publication Data
US 2022/0399146 A1    Dec. 15, 2022

Related U.S. Application Data

(60) Provisional application No. 63/208,776, filed on Jun. 9, 2021.

(51) Int. Cl.
| | |
|---|---|
| *H01F 7/06* | (2006.01) |
| *G01R 33/00* | (2006.01) |
| *G01R 33/26* | (2006.01) |
| *H01F 27/28* | (2006.01) |

(52) U.S. Cl.
CPC ......... *H01F 7/064* (2013.01); *G01R 33/0017* (2013.01); *G01R 33/26* (2013.01); *H01F 27/2804* (2013.01)

(58) Field of Classification Search
CPC ..... G01R 33/0017; G01R 33/26; H01F 7/064; H01F 7/2804
See application file for complete search history.

(56) References Cited

U.S. PATENT DOCUMENTS

| | | | |
|---|---|---|---|
| 11,269,027 B2* | 3/2022 | Mohseni | G01R 33/26 |
| 2013/0197838 A1 | 8/2013 | Simola et al. | |
| 2015/0219732 A1 | 8/2015 | Diamond et al. | |
| 2020/0069293 A1 | 3/2020 | Julian et al. | |
| 2021/0244329 A1* | 8/2021 | Ledbetter | A61B 5/248 |
| 2021/0293913 A1* | 9/2021 | Mifune | G01R 33/26 |

FOREIGN PATENT DOCUMENTS

| | | |
|---|---|---|
| JP | 2000037362 A | 2/2000 |
| WO | 2021028620 A1 | 2/2021 |

OTHER PUBLICATIONS

International Search Report and Written Opinion for PCT Application No. PCT/US2022/032810, mailed Sep. 27, 2022; 11 pages.

\* cited by examiner

*Primary Examiner* — Gregory H Curran

(57) ABSTRACT

Various embodiments comprise a magnetic field compensation system. In some examples, the system comprises one or more coil drivers, magnetic field coils, and one or more magnetic field sensors. The one or more coil drivers supply a current to the magnetic field coils to generate a magnetic field. The magnetic field coils receive the current and generate the magnetic field. The magnetic field coils may be arranged in an array. The magnetic field coils individually comprise at least one coil trace pattern that encloses an area. The one or more magnetic field sensors measure the magnetic field generated by the magnetic field coils at a location proximate to the magnetic field coils.

20 Claims, 10 Drawing Sheets

MODULAR MAGNETIC FIELD COMPENSATION COIL ARRAY

RELATED APPLICATIONS

This Patent Application claims the benefit of and priority to U.S. Provisional Patent Application 63/208,776 entitled, "MODULAR COMPENSATION COILS FOR OPTICALLY-PUMPED MAGNETOMETER MAGNETOENCEPHALOGRAPHY (OPM MEG)" which was filed on Jun. 9, 2021, and which is hereby incorporated by reference in its entirety into this Patent Application.

BACKGROUND

Optically-Pumped Magnetometers (OPMs) are a magnetic field sensor technology that can be used to measure bio-magnetic activity in applications like Magnetoencephalography (MEG) and Magnetocardiography (MCG). MEG source analysis processes the OPM signals to build a model of the target magnetic field and source. When in use, the OPM sensors are often placed within a magnetically shielded enclosure to isolate the OPM sensors from background magnetic fields like the Earth's magnetic field and the field from magnetic interference. For example, the magnetically shielded enclosure may comprise a Faraday Cage and material with high magnetic permeability. To further reduce the background magnetic field, large magnetic coils are often positioned inside the magnetically shielded enclosure near the OPM sensors to generate additional magnetic fields and null the background magnetic fields and magnetic gradients in the magnetically shielded enclosure around the OPM sensors. A field processor uses the input from some or all of the OPM sensors to generate outputs for the field and gradient coils. Unfortunately, the large magnetic coils are cumbersome to build and use.

Overview

This Overview is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Various embodiments of the present technology relate to solutions for magnetic field sensing and generation. Some embodiments comprise a magnetic field compensation system. The system comprises one or more coil drivers, magnetic field coils, and one or more magnetic field sensors. The one or more coil drivers supply a current to the magnetic field coils to generate a magnetic field. The magnetic field coils receive the current and generate the magnetic field. The magnetic field coils may be arranged in an array. The magnetic field coils individually comprise at least one coil trace pattern that encloses an area. The one or more magnetic field sensors measure the magnetic field generated by the magnetic field coils at a location proximate to the magnetic field coils.

Some embodiments comprise a method to of operating a magnetic field compensation system. The method comprises one or more coil drivers supplying a current to magnetic field coils to generate a magnetic field. The method continues by the magnetic field coils receiving the current and generating the magnetic field. The magnetic field coils may be arranged in an array and may comprise at least one coil trace pattern that encloses an area. The method continues by one or more magnetic field sensors measuring the magnetic field generated by the magnetic field coils at a location proximate to the magnetic field coils.

DESCRIPTION OF THE DRAWINGS

Many aspects of the disclosure can be better understood with reference to the following drawings. The components in the drawings are not necessarily drawn to scale. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

Figure 1:
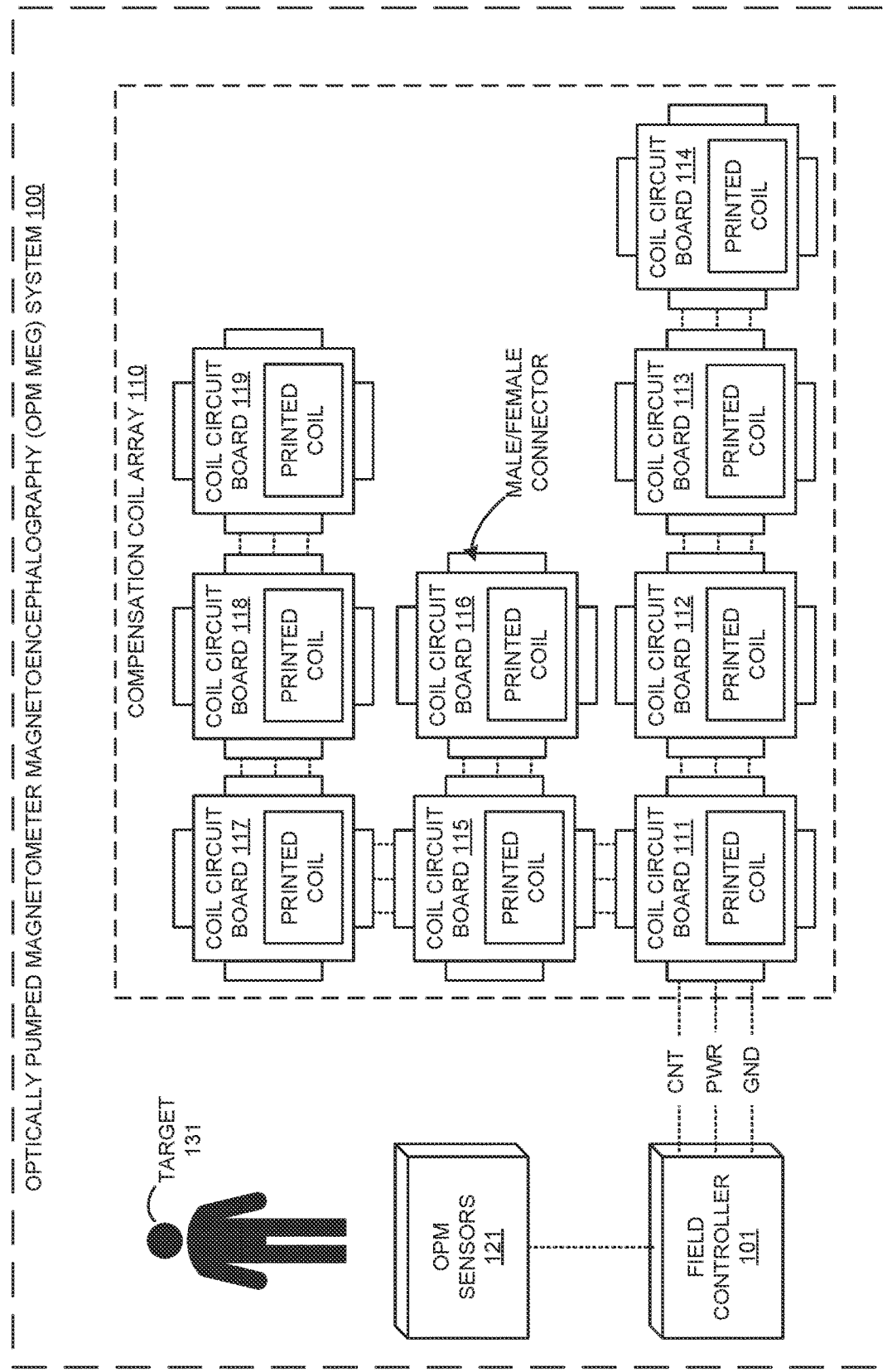
FIG. 1 illustrates an exemplary Optically Pumped Magnetometer Magnetencephalography (OPM MEG) system to mitigate a background magnetic field.

The drawings have not necessarily been drawn to scale. Similarly, some components or operations may not be separated into different blocks or combined into a single block for the purposes of discussion of some of the embodiments of the present technology. Moreover, while the technology is amendable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

The following description and associated figures teach the best mode of the invention. For the purpose of teaching inventive principles, some conventional aspects of the best mode may be simplified or omitted. The following claims specify the scope of the invention. Note that some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

FIG. 1 illustrates Optically Pumped Magnetometer Magnetencephalography (OPM MEG) system 100 to mitigate a background magnetic field. OPM MEG system 100 drives compensation coil array 110 to emit magnetic fields to null background magnetic fields and/or produce a magnetic field landscape with a desired offset and curvature. OPM MEG system 100 comprises magnetic field controller 101, compensation coil array 110, OPM sensors 121, and target 131. Compensation coil array 110 comprises modular coil circuit boards 111-119. Coil circuit boards 111-119 comprise male/female pin/socket connectors that allow coil circuit boards 111-119 to connect to one another, driver circuitry to implement instructions received from field controller 101, and printed coils to generate the desired magnetic field.

Various examples of system operation and configuration are described herein. In some examples, coil circuit boards 111-119 couple to each other by their connectors to form compensation coil array 110. Coil circuit board 111 couples to field controller 101. Field controller 101 supplies power (PWR) to coil circuit boards 111-119 over coil circuit board 111. Field controller 101 supplies control signaling (CNT) to coil circuit boards 111-119 over coil circuit board 111. For example, field controller 101 may receive magnetic field readings from OPM sensors 121 and responsively generate control signaling that directs coil circuit boards 111-119 to generate a nulling magnetic field that enables OPM sensors 121 to effectively measure a target magnetic field generated by neuron activity of target 131. The driver circuitry of coil circuit boards 111-119 individually control the voltage and/or current for respective printed coils based on the control signaling from field controller 101. The driver circuitry of coil circuit boards 111-119 supply current to their respective printed coils. The printed coils of coil circuit boards 111-119 receive the current and generate a nulling magnetic field for OPM MEG system 100 based on the voltage and/or current.

Advantageously, field controller 101 sets the power to each coil individually to generate magnetic fields which null magnetic field noise in the proximity of OPM sensors 121 and target 131. Moreover, coil circuit boards 111-119 easily couple together to form compensation coil array 110.

Coil circuit boards 111-119 can be arranged in different geometries in array 110 due to their modular nature. The magnetic field in a volume in the vicinity of coils 111-119 can be controlled dynamically. For example, it might be desirable to create a homogenous magnetic field in a certain volume. The currents in individual ones of coils 111-119 can then be adjusted to maximize the field homogeneity in that volume. The volume of interest can be chosen at different locations. Coil circuit boards 111-119 can also be used to generate magnetic field patterns, which in-turn can be used to determine spatial characteristics of OPM sensors 121. In some examples, the spatial characteristics comprise the locations of OPM sensors 121. In some examples, the spatial characteristics comprise the orientations of OPM sensors 121. In some examples, comprise the locations and the orientations of OPM sensors 121. By determining the spatial characteristics of OPM sensors 121, coil circuit boards 111-119 may adjust the location of the volume with field homogeneity to track OPM sensors 121. For example, target 131 may move around a room with OPM sensors 121 and coil circuit boards 111-119 may adjust the location of the volume of interest accordingly.

For the implementation of OPM MEG system 100, for example, a homogenous zero-field environment can be created. OPM sensors 121 can be used to dynamically steer the field zero and gradient field environment to follow the location of target 131. The positions and orientations of at least some of the OPMs of OPM sensors 121 can be determined by applying signals to coil circuit boards 111-119. Field controller 101 then determines the currents to be generated in the magnetic field coils to optimize the field zero at the location of the target 131 dynamically, even when the subject is moving locations.

In some examples, compensation coil array 110, OPM sensors 121, and target 131 may be located in a magnetically shielded enclosure. Each individual magnetic coil of coil circuit boards 111-119 emits a magnetic field to form the overall nulling magnetic field pattern within the magnetically shielded enclosure. OPM sensors 121 detect the nulling magnetic field and generate signals that characterize the nulling magnetic field. OPM sensors 121 transfer the signals to field controller 101. Field controller 101 processes the signals from OPM sensors 121 to generate data that characterizes the magnetic field pattern. For example, the field controller 101 may build and maintain a three-dimensional model of the nulling magnetic field.

In some examples, field controller 101 receives magnetic field readings from OPM sensors 121 that indicate magnetic field noise in the vicinity of target 131 and OPM sensors 121. Field controller 101 generates and transfers instructions to cause the driver circuitry of coil circuit boards 111-119 to individually control the voltage and/or current for each one of modular coil circuit boards 111-119 to generate a nulling magnetic field that mitigates the magnetic field noise reported by OPM sensors 121. The individual controls include coil voltage control, current control, and the like. Field controller 101 controls the current and/or voltage of each coil independently. For example, the field controller 101 may transfer instructions to the driver circuitry to increase the strength of the magnetic field generated by coil circuit board 111 and decrease the strength of the magnetic field generated by coil circuit board 116. Modular coil circuit boards 111-119 emit magnetic fields to null background magnetic fields in the proximity of target 131 in response to control signaling received from field controller 101. Alternatively, coil circuit boards 111-119 may produce a magnetic field landscape with a desired offset and curvature in the proximity of target 131 and OPM sensors 121. For example, field controller 101 may calculate multiple interacting bias fields using OPM sensors 121 to optimize the magnetic null in the vicinity of target 131 and may drive control coil circuit boards 111-119 to generate the magnetic null. Field controller 101 uses additional readings from OPM sensors 121 to dynamically adjust magnetic fields generated by coil circuit boards 111-119.

In some examples, coil circuit boards 111-119 identify themselves to field controller 101 by coil ID along with coil status and history. Coil circuit boards 111-119 identify themselves to their neighbors by coil ID and report their coil IDs and their neighbor coil IDs to field controller 101. The reports indicate whether the connection is the left, right, top, or bottom connection and the coil ID of the neighbor. Field controller 101 maintains a model of the architecture of compensation coil array 110 based on these reports. Field controller 101 may individually control the operation of coil circuit boards 111-119 based on the architecture of compensation coil array 110.

Figure 2:
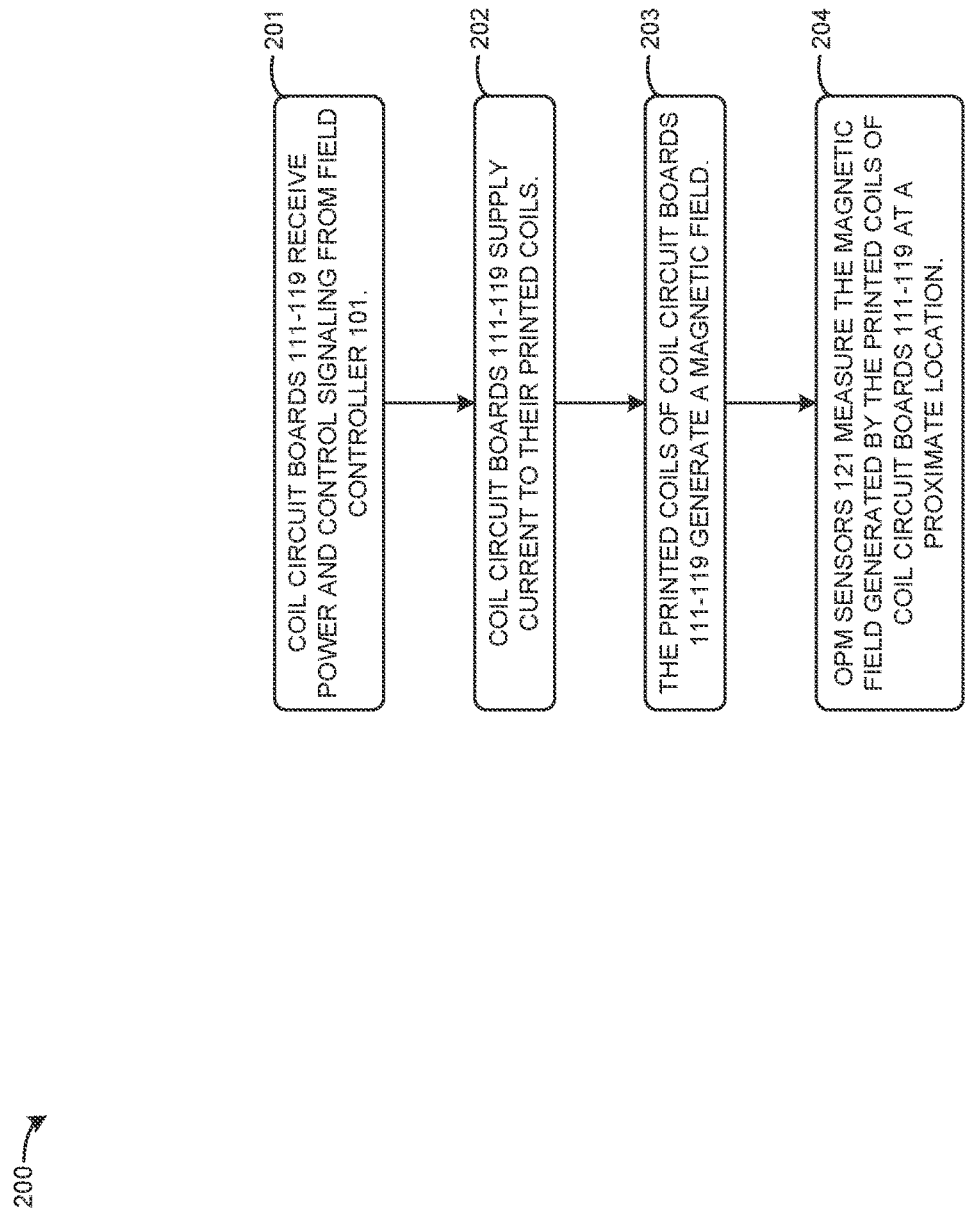
FIG. 2 illustrates an exemplary operation of the OPM MEG system to null the background magnetic field.

FIG. 2 illustrates process 200. Process 200 comprises an exemplary operation of OPM MEG system 100 to null a background magnetic field. The operation of process 200 and OPM MEG system 100 may differ in other examples. In operation, coil circuit boards 111-119 receive power and control signaling from field controller 101 (step 201). Coil circuit boards 111-119 supply current to their printed coils (step 202). The printed coils of coil circuit boards 111-119 generate a magnetic field (step 203). OPM sensors 121 measure the magnetic field generated by the printed coils of coil circuit boards 111-119 at a proximate location (step 204).

Figure 3:
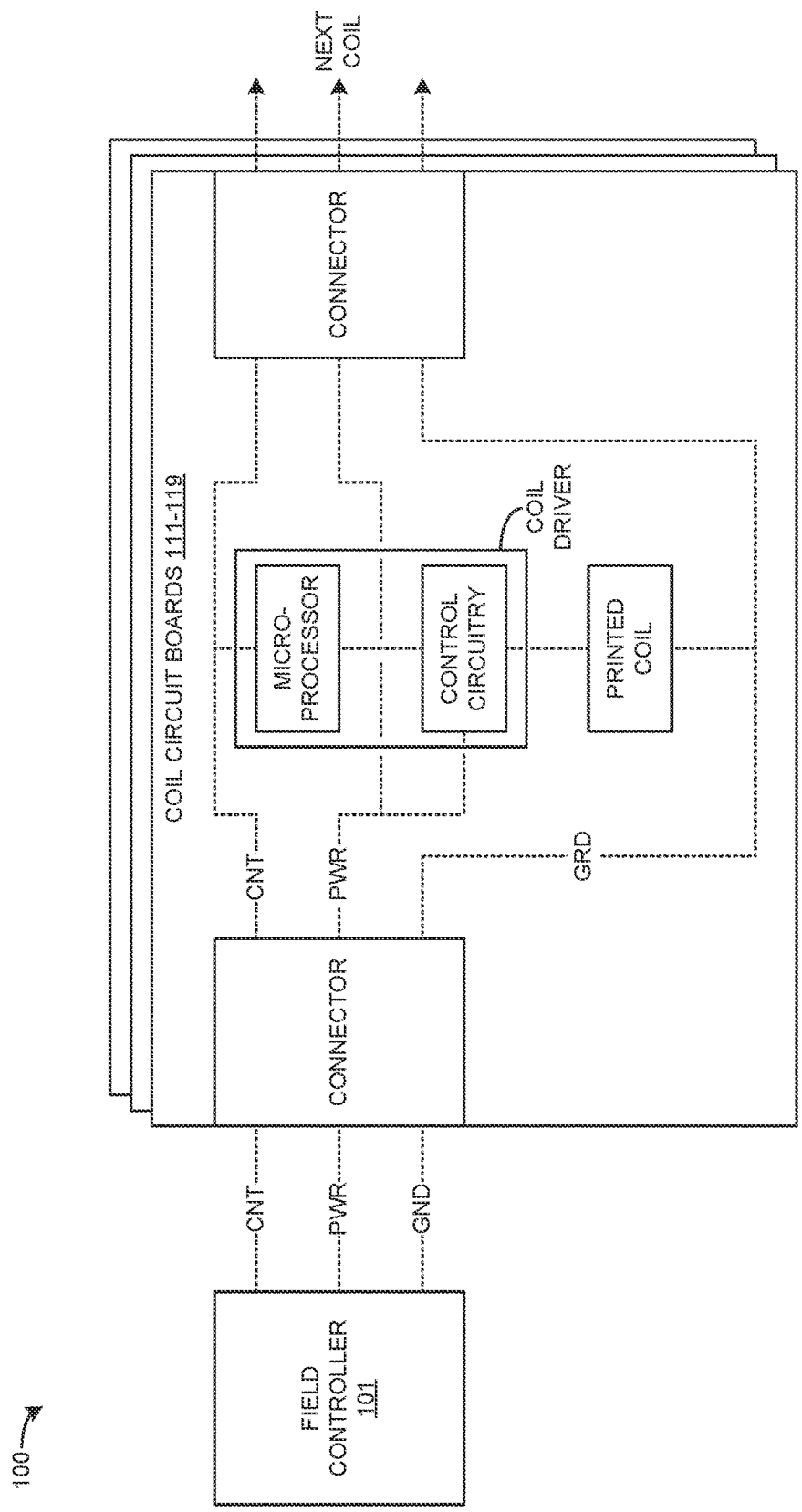
FIG. 3 illustrates exemplary coil circuit boards in the OPM MEG system.

FIG. 3 illustrates modular coil circuit boards 111-119 and field controller 101. Coil circuit boards 111-119 comprises connectors, a microprocessor, voltage/current controller, and a printed coil. The microprocessor and voltage/current controller forms a coil driver to execute control instructions generated by field controller 101 and supply corresponding current to the printed coil to generate a magnetic field according to the control instructions. In this example, the coil circuit boards 111-119 comprise printed circuit boards. Typically, the printed circuit boards are rectangular, however, the shape of the printed circuitry boards is not limited. For example, the printed circuit boards may be triangular, hexagonal, circular, and the like. The connector in coil circuit board 111 is coupled to field controller 101 over control, power, and ground links. The connectors in coil circuit boards 111-119 are connected to each other over control, power, and ground links as shown in FIG. 1. In other examples, the connection arrangement of coil circuit boards 111-119 may be different. Field controller 101 supplies power to coil circuit boards 111-119 that may be delivered by an alternating current or direct current and at high voltage or low voltage. The connectors, microprocessor, and voltage/current controller are attached to the circuit board. The coils and links are printed on the circuit board. The printed coil comprises a trace line printed on the circuit board that encloses an area and is configured to generate a magnetic field. The connectors are linked to each other and the microprocessor over a control bus. The microprocessor and the voltage/current controller are linked to each other. The connectors and the voltage/current controller are linked over a power bus and a ground bus. The voltage/current controller and the printed coil are linked to each other. The connectors and the printed coil are linked to the ground bus that provides an electrical ground for the internal components of coil circuit boards 111-119.

The connectors comprise metallic male/female type couplings like pins and sockets. If the connector on the left is male, the connector on the right is female. If the connector on the left is female, the connector on the right is male. Thus, the connectors of different modular coil circuit boards 111-119 may be easily snapped together by hand. In some examples, the connectors of coil circuit boards 111-119 may connect to each other over ribbon cables and/or flat flex cables. For example, a cable may plug into a connector of coil circuit board 111 and into a connector of coil circuit board 112 to link the two boards. The connectors include links for control, power, and ground. An additional connector like the left connector could be placed at the top of the circuit board. An additional connector like the right connector could be placed at the bottom of the circuit board. In some examples, coil circuit boards 111-119 comprise an adhesive side that allows coil circuit boards 111-119 to be secured to vertical surfaces. For example, coil circuit boards 111-119 may comprise peel and stick pads to mount coil circuit boards 111-119 to the side walls of a magnetically shielded enclosure.

The microprocessors in coil circuit boards 111-119 comprise Central Processing Units (CPUs), Graphical Processing Units (GPUs), Application Specific Integrated Circuit (ASICs), Field Programmable Gate Array (FPGAs), Digital Signal Processor (DSPs), or other types of processing circuitry. The voltage/current controllers comprise electronic components to regulate the voltage and/or current based on control signals generated by field controller 101. The printed coil comprises metallic lines embedded on the circuit board that generate a magnetic field when supplied with electrical power. As stated above, the metallic lines form a trace pattern that encloses an area on coil circuit boards 111-119 with the goal of producing a magnetic field.

Field controller 101 transfers control signals to the microprocessors in coil circuit boards 111-119 that indicate the amount of voltage and/or current to be supplied to their printed coils. The microprocessors receive and execute the control signals and responsively direct the voltage/current controller to supply the indicated amount of voltage and/or current to the printed coil. The printed coils receive the current and generate a specific magnetic field responsive to the voltage and/or current. The specific magnetic field interacts with the magnetic fields of other modular coils to mitigate the background magnetic field in a magnetically shielded enclosure. Coil circuit boards 111-119 may be placed in various locations throughout the magnetic enclosure or may be embedded into the walls of the magnetically shielded enclosure to create compensation coil array 110. In some examples coil circuit boards 111-119 may include WiFi and/or Bluetooth cards that allow coil circuit boards 111-119 to wirelessly receive control signaling from field controller 101. In some examples coil circuit boards 111-119 may include Ethernet cards that allow coil circuit boards 111-119 to receive control signaling from field controller 101 via an Ethernet link.

In some examples, modular coil circuit boards 111-119 send different amounts of current to their printed coils to generate multiple magnetic fields with varying field strengths. The multiple magnetic fields with varying field strengths interact to form an overall magnetic field with a desired shape, strength, and gradient. The relationship between the amount of current supplied to a first coil circuit board and the amount of current supplied to a second coil circuit board is referred to as a current ratio. Field controller 101 may adjust the current ratios of coil circuit boards 111-119 based on the geometric arrangement of compensation coil array 110.

In some examples, modular coil circuit boards 111-119 comprise fiducial marks and Quick Response (QR) codes on their surface that individually identify coil circuit boards 111-119. The QR codes may be optically scanned by a device (e.g., smart phone or tablet) to obtain coil IDs for coil circuit boards 111-119. The device may then transfer the coil IDs to field controller 101. Field controller 101 may determine the specific geometry of coil circuit boards 111-119 in compensation coil array 110 based on the coil IDs received from the device.

Figure 4:
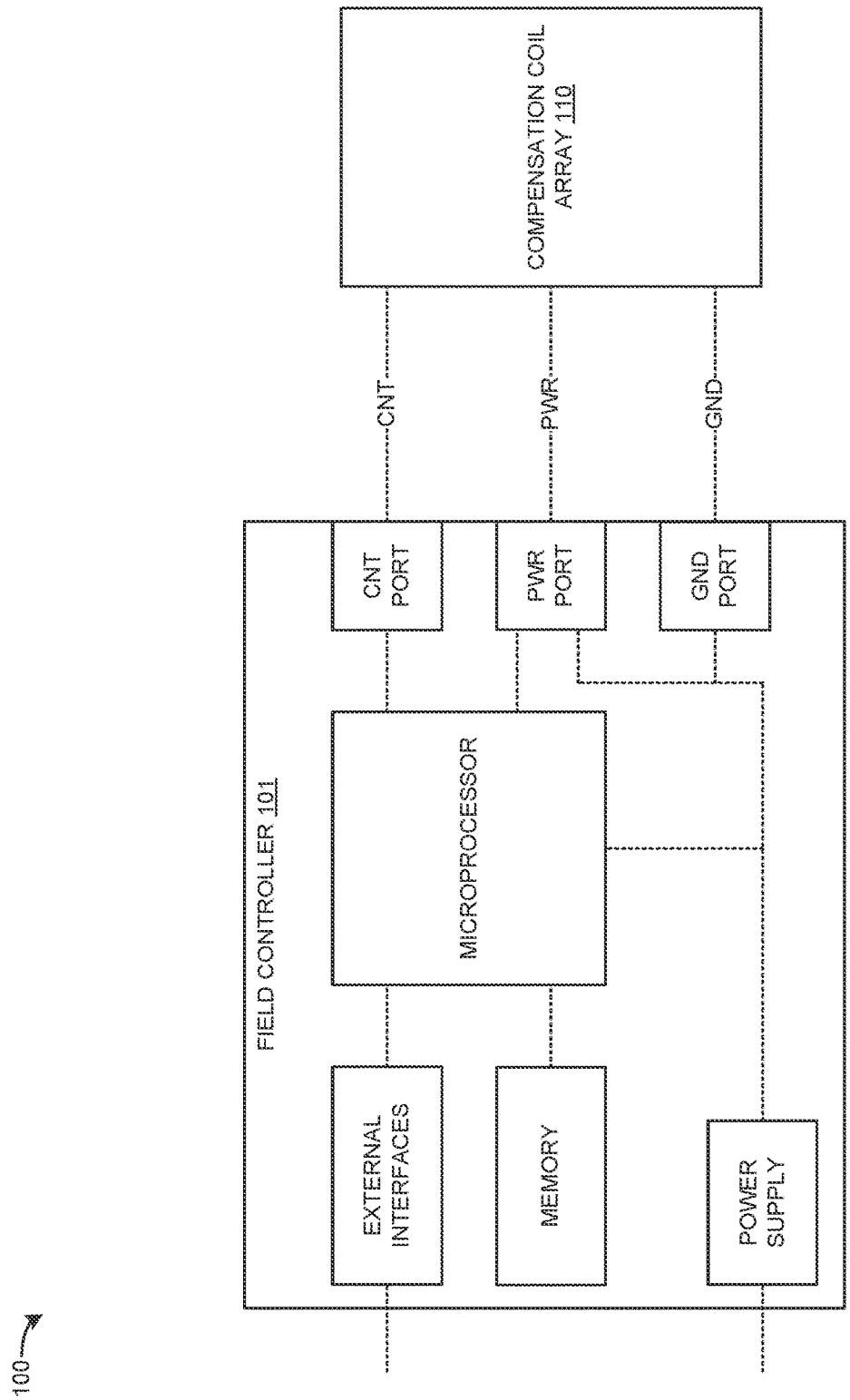
FIG. 4 illustrates an exemplary magnetic field controller in the OPM MEG system.

FIG. 4 illustrates field controller 101 and compensation coil array 110. Field controller 101 comprises a control port, a power port, a ground port, a microprocessor, external interfaces, memory, and a power supply. Field controller 101 is coupled to compensation coil array 110 over control, power, and ground links. The microprocessor in field controller 101 comprises CPU, GPU, ASIC, FPGA, DSP, and/or the like. The memory in field controller 101 comprises Random Access Memory (RAM), flash circuitry, disk drives, and/or the like. The external interfaces in field controller 101 comprise transceiver circuitry that allows the microprocessor in field controller 101 to communicate with external systems like OPM sensors 121, smart phones, computers, and the like. The power supply in field controller 101 comprises filters, transformers, rectifiers, and the like to provide power to the internal components of field controller 101 and to compensation coil array 110. The control, power, and ground ports comprise metallic male/female type couplings like pins and sockets or cabling to transfer control signaling, power, and provide an electrical ground to compensation coil array 110. The memories store software like operating systems, user applications, field generation applications, coil circuit board applications, and the like. The microprocessor retrieves the software from the memories and executes the software to drive the operation of field controller 101.

In some examples, the external interfaces in field controller 101 receives background magnetic field readings from OPM sensors 121. The background magnetic field readings indicate magnetic noise that needs to be mitigated by compensation coil array 110. The external interfaces transfer the magnetic field readings to the microprocessor in field controller 101. The control port receives architecture reports from compensation coil array 110 that indicate coil IDs for coil circuit boards 111-119, inter-coil connections between coil circuit boards 111-119, whether the inter-coil connections are the left, right, top, or bottom connection, and the coil ID of the neighboring coils. The control port transfers the coil IDs to the microprocessor. In some examples, the external interfaces receive coil IDs that indicate individual ones of modular coil circuit boards 111-119 that were obtained via optical scanning. For example, the optically scanned coil IDs may be obtained through QR codes or other types of fiduciary marks on coil circuit boards 111-119. The microprocessor may execute the field generation applications stored in the memory to determine the architecture of compensation coil array 110 based on the coil IDs and inter-coil connections of coil circuit boards 110-119.

The microprocessor in field controller 101 executes the field generation applications to generate control signaling for compensation coil array 110 based on the magnetic field readings from OPM sensors 121 and the architecture of compensation coil array 110. The control signaling controls the voltage and/or current for each one of modular coil circuit boards 111-119 in compensation coil array 110 to generate a nulling magnetic field. The control signaling may indicate a current ratio to be used for compensation coil array 110. The microprocessor transfers individually addressed control signaling to compensation coil array 110 over the control link. The control signaling directs coil circuit boards 111-119 to generate magnetic fields that mitigate the noise of the background magnetic field, generate a magnetic field with a desired curvature and offset, or generate some other type of magnetic field. Once the nulling field is generated, the microprocessor may receive additional magnetic field readings from OPM sensors 121. The microprocessor uses the additional magnetic field readings to generate and transfer updated control signaling to compensation coil array 110 thereby allowing the field controller to tune the nulling background magnetic field in real or near-real time. Additionally, the microprocessor may use the additional magnetic field readings to generate and transfer updated control signaling to move a volume comprising the magnetic field generated by coil array 110 to a new location.

Figure 5:
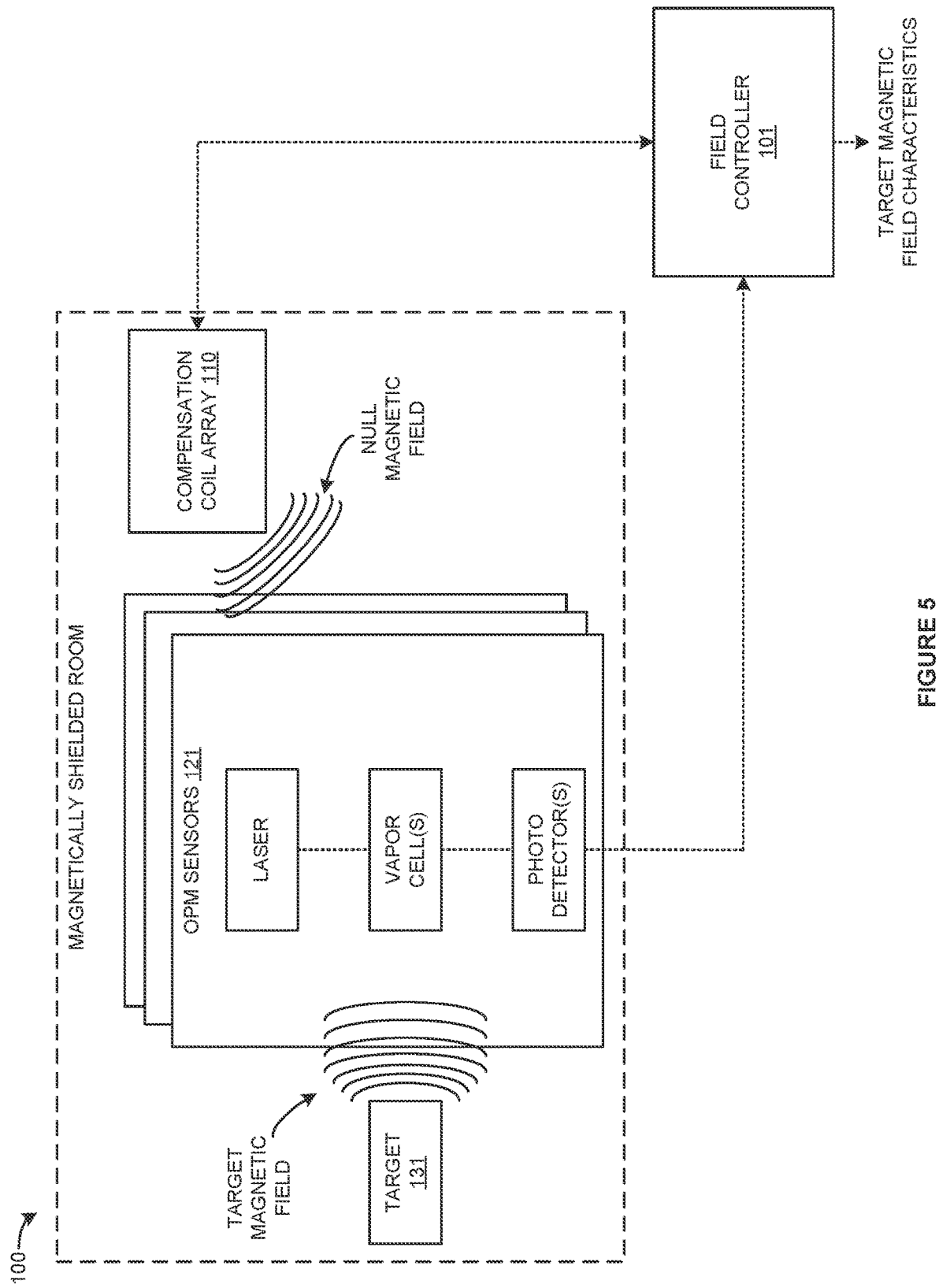
FIG. 5 illustrates exemplary OPM sensors in the OPM MEG system.

FIG. 5 illustrates a magnetically shielded enclosure that comprises target 131, OPM sensors 121, and compensation coil array 110. OPM sensors 121 and compensation coil array 110 are coupled to field controller 101 which is outside of the magnetically-shielded enclosure. OPM sensors 121 comprise at least one laser, vapor cell, and photodetector. OPM sensors 121 may include signal processors and other electronics. The vapor cell(s) contain an alkali metal vapor like rubidium. Alternative cells with alkalis, helium, and nitrogen-vacancy centers could be used instead of or along with the vapor cells. The vapor cell(s) are biased by coil circuit boards 111-119. The laser may include additional lasers. In other examples, OPM sensors 121 may comprise different types of magnetometers. It should be appreciated that the specific type of magnetic sensors used in relation to compensation coil array 110 is not limited.

In operation, coil circuit boards 111-119 of compensation coil array 110 generate magnetic fields responsive to control signaling from field controller 101 to reduce background magnetic fields (or to create a desired background magnetic field) inside the magnetically shielded enclosure—especially the part of the enclosure where OPM sensors 121 and target 131 are positioned. Coil circuit boards 111-119 generate a nulling magnetic field at the locations of the vapor cells in OPM sensors 121. The laser emits a pump beam that is circularly polarized at a resonant frequency of the vapor to polarize the atoms. The laser beam enters the vapor cells where quantum interactions with the atoms alter the intensity/polarization of the probe beam by amounts that correlate to the magnetic field.

The photodetector detects the laser beam after these alterations by the vapor atoms. The photodetector generates and transfers corresponding analog electronic signals that characterize the magnetic field. In some examples, a signal processor may filter, amplify, digitize, or perform other tasks on the analog electronic signals. The photodetectors or signal processors transfer an electronic signal that carries the data to field controller 101. Field controller 101 processes the electronic signal to generate and transfer data that characterizes the nulling magnetic field. Field controller 101 typically processes OPM data from multiple OPMs to model the magnetic field in three dimensions. In some examples, field controller 101 adjusts, moves, or otherwise changes the nulling magnetic fields and gradient magnetic fields generated by coil circuit boards 111-119 in response to the output data from OPM sensors 121.

Figure 6:
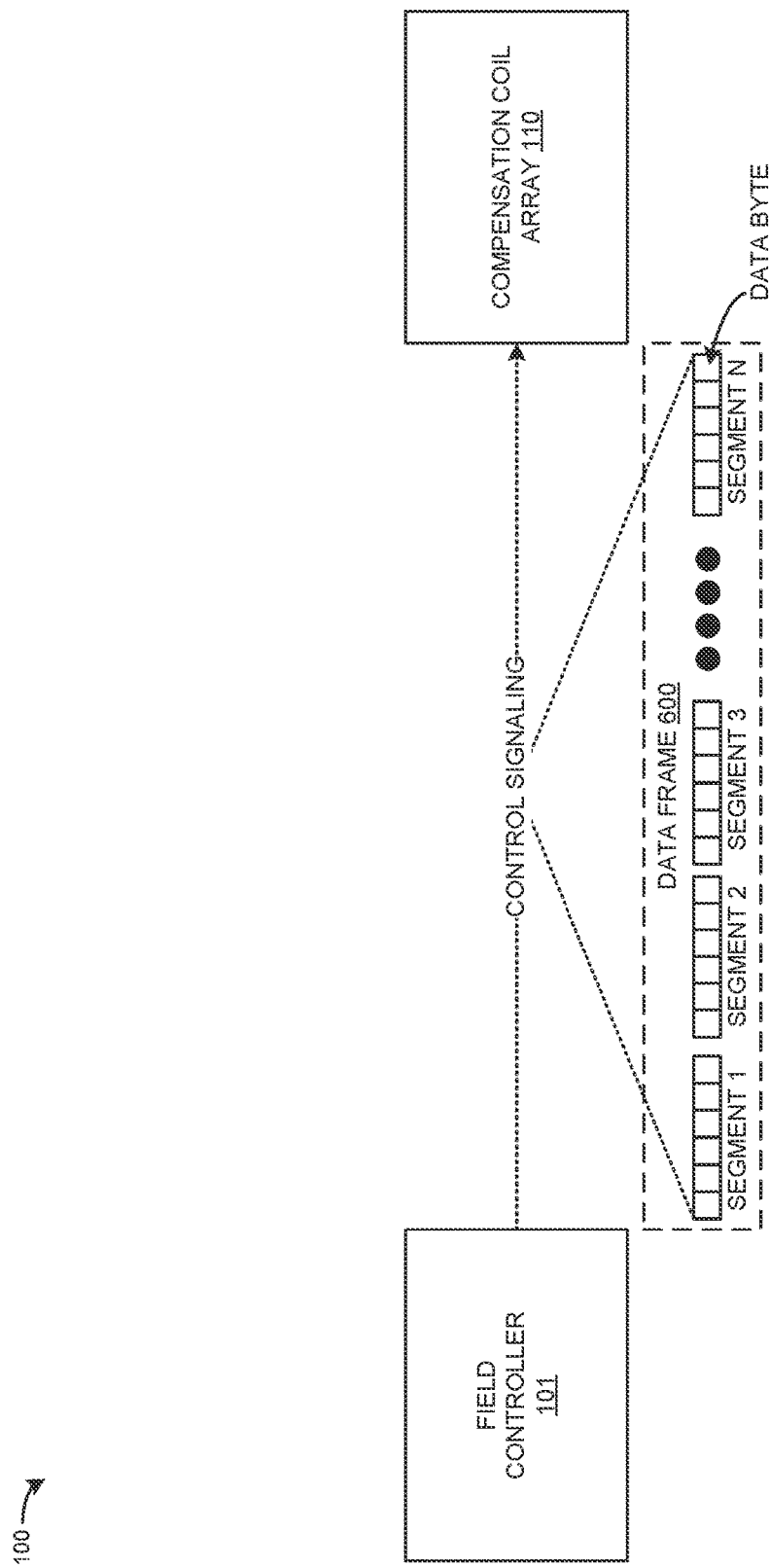
FIG. 6 illustrates exemplary control signaling in the OPM MEG system.

FIG. 6 illustrates field controller 101, compensation coil array 110, and data frame 600. In this example, field controller 101 transfers control signaling that comprises data frame 600 to compensation coil array 110. Data frame 600 comprises a data structure similar to an image file. Data frame 600 comprises data bytes that are grouped into data segments. The data segments of data frame 600 comprise individual coil control instructions and correspond to individual ones of coil circuit boards 111-119. For example, the first 24 bytes (e.g., segment 1) of data frame 600 may comprise coil control instructions for coil circuit board 111 and the next 24 bytes (e.g., segment 2) of data frame 600 may comprise coil control instructions for coil circuit board 112 and so on until each one of coil circuit boards 111-119 have been addressed coil control instructions. In other examples, the individual coil control instructions in data frame 600 may be structured differently. The coil control instructions in data frame 600 may include delay commands to synchronize the operation of coil circuit boards 111-119 so that coil circuit boards 111-119 simultaneously implement their coil control instructions. The coil control instructions in data frame 600 may be comprise a current ratio based on the geometric arrangement of array 110.

Figure 7:
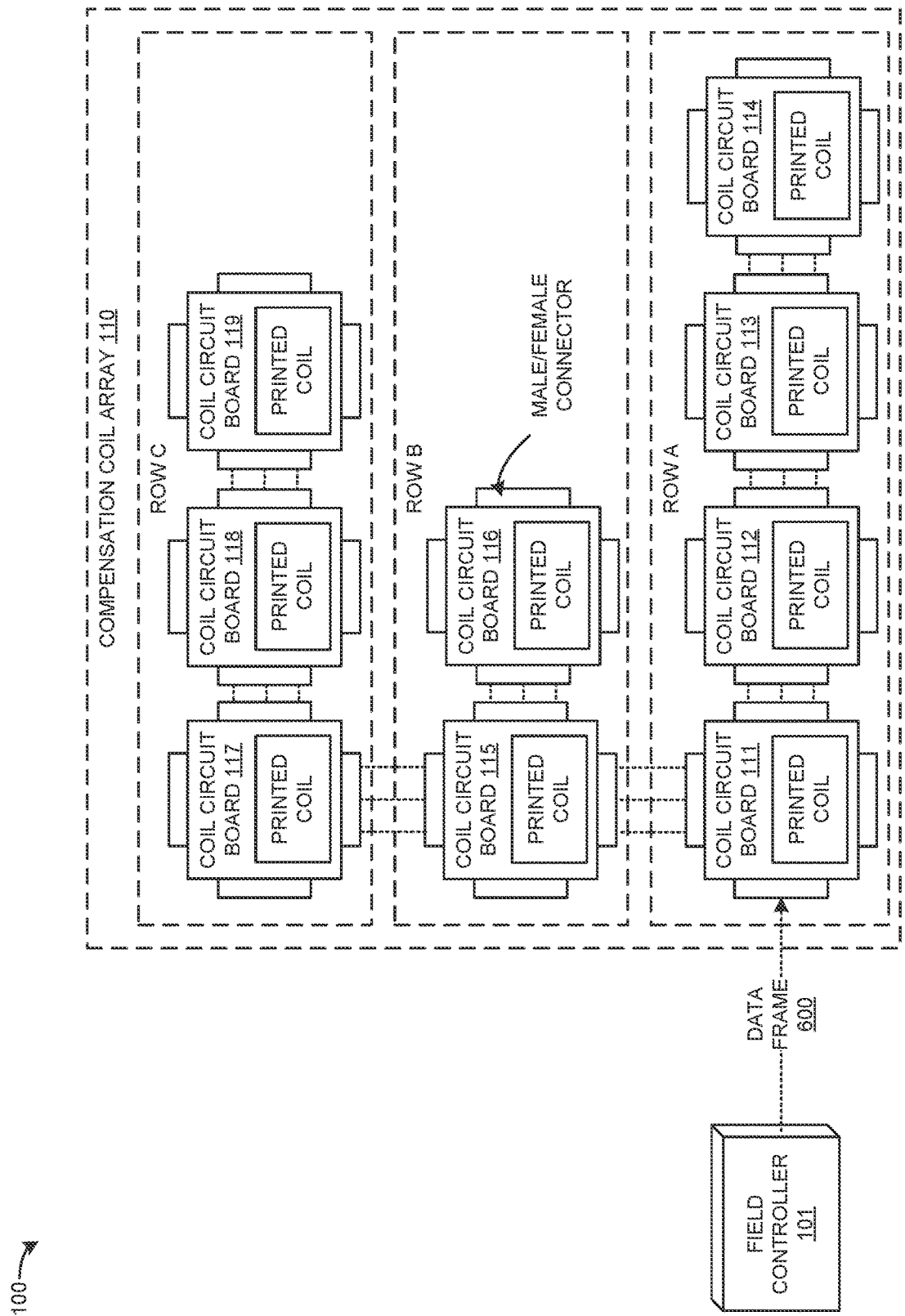
FIG. 7 illustrates an exemplary control signaling distribution scheme in the OPM MEG system.

FIG. 7 further illustrates field controller 101, compensation coil array 110, and data frame 600. In this example, coil circuit boards 111-119 in compensation coil array 110 are organized into rows. Coil circuit boards 111-114 comprise row A, coil circuit boards 115-116 comprise row B, and coil circuit boards 116-119 comprise row C. In this example, the data segments of data frame 600 correspond to coil circuit boards 111-119 and to rows A-C. Field controller 101 transfers data frame 600 to coil circuit board 111 to drive compensation coil array 110 to create a nulling magnetic field. Coil circuit board 111 parses the segment from data frame 600 that corresponds to row A to retrieve its coil control instructions and the coil instructions for coil circuit boards 112-114. Coil circuit board 111 transfers the remainder of data frame 600 that corresponds to rows B and C to coil circuit board 115. Coil circuit board 111 parses the data frame segment that corresponds to row A to retrieve its coil control instruction. Coil circuit board 111 transfers the remainder of the data frame segment that corresponds to row A to coil circuit boards 112. Coil circuit boards 112-119 receive, parse, and transfer data segments of data frame 600 in a manner similar to coil circuit board 111 to distribute the coil instructions from field controller 101. Coil circuit boards 111-119 use the coil control instructions from data frame 600 to generate a nulling magnetic field.

Figure 8:
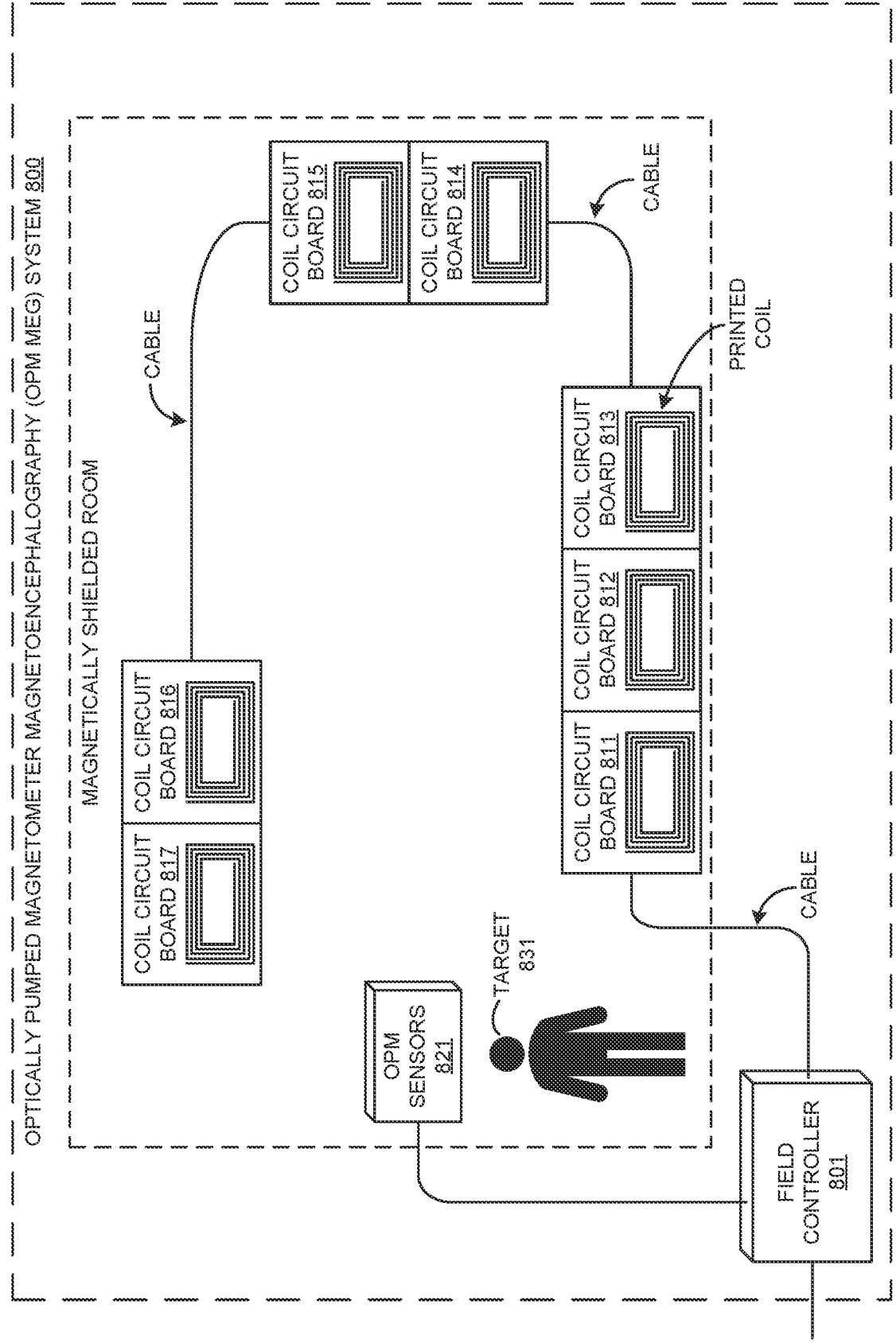
FIG. 8 illustrates an exemplary OPM MEG system to mitigate a background magnetic field.

FIG. 8 illustrates OPM MEG system 800. OPM MEG system 800 comprises an example of OPM MEG system 100, however OPM MEG system 100 may differ. OPM MEG system 800 comprises field controller 801, coil circuit boards 811-817, OPM sensors 821, and target 831. Field controller 801 transfers control instructions to driver circuitry in coil circuit boards 811-817. The driver circuitry in coil circuit boards 811-817 receive and execute the control instructions and transfer current to the printed coils of coil circuit boards 811-817 based on the control instructions. The printed coils receive the current and emit magnetic fields to null background magnetic fields and/or produce a magnetic field landscape with a desired offset and curvature. Coil circuit boards 811-817 comprise male/female pin/socket connectors that allow coil circuit boards 811-817 to connect to one another or to connect to cables. Coil circuit boards 811-817, OPM sensors 821, and target 831 are positioned within a magnetically shielded enclosure. Field controller 801 is positioned outside of the magnetically shieled enclosure. OPM sensors 821 are positioned proximate to target 831 and report magnetic field measurements to field controller 801 over a cable.

Coil circuit boards 811-817 comprise rectangular printed circuit boards, however differently shaped circuit boards could be used. For example, coil circuit boards 811-817 could be circular, hexagonal, or some other type of shape. In this example, coil circuit boards 811-817 are printed circuit boards, however in other example coil circuit boards may comprise a different construction. For example, coil circuit boards 811-817 may comprise plastic panels that house circuitry and coils to generate the nulling magnetic field. Coil circuit boards 811-817 comprise printed coils to generate the nulling magnetic field. The printed coils are rectangular, however other coil shapes and/or coil designs may be used in other examples. The printed coils are printed onto coil circuit boards 811-817 forming a trace line that encloses an area and are configured to generate magnetic fields in response to receiving current. In other examples, the coils may be wound onto coil circuit boards 811-817 or adhered to coil circuit boards 811-817 in some other manner.

Coil circuit board 811 is coupled to field controller 801 over a cable. The cables that interconnect the various elements of OPM MEG system 800 may comprise sheathed metallic wires. Coil circuit boards 811-813, 814-815, and 816-817 are coupled together by their male/female pin socket connectors. Coil circuit board 813 is coupled to coil circuit board 814 over a cable. Similarly, coil circuit board 815 is coupled to coil circuit board 816 by another cable. The cables transfer control signaling and power from field controller 801 to and between coil circuit boards 811-817. In some examples, the cables may comprise flat ribbon cables or other types of cables.

Coil circuit boards 811-813 are positioned on the floor of the magnetically shielded enclosure, coil circuit boards 814-815 are positioned on a wall of the magnetically shielded enclosure, and coil circuit boards 816-817 are positioned on the ceiling of the magnetically shielded enclosure. Coil circuit boards 811-817 may use peel-and-stick adhesive pads, plastic clips, hook-and-loop fasteners, and/or other types of mounting mechanisms to secure themselves to the floor, walls, and ceiling of the magnetically shielded enclosure. It should be noted that the number of coil circuit boards used in OPM MEG system 800 is not limited. For example, many more coil circuit boards could be used in OPM MEG system 800 to fully or partially tile the floor, walls, and ceiling of the magnetically shielded enclosure. In some examples, coil circuit boards 811-817 are constructed in a manner so that they are durable enough to withstand the pressure of being walked on. For example, target 831 may walk on coil circuit boards 811-813 when entering the magnetic shielded enclosure without damaging the functionality of coil circuit boards 811-813. In other examples, coil circuit boards 811-817 may comprise a protective casing to mitigate or otherwise prevent damage.

Figure 9:
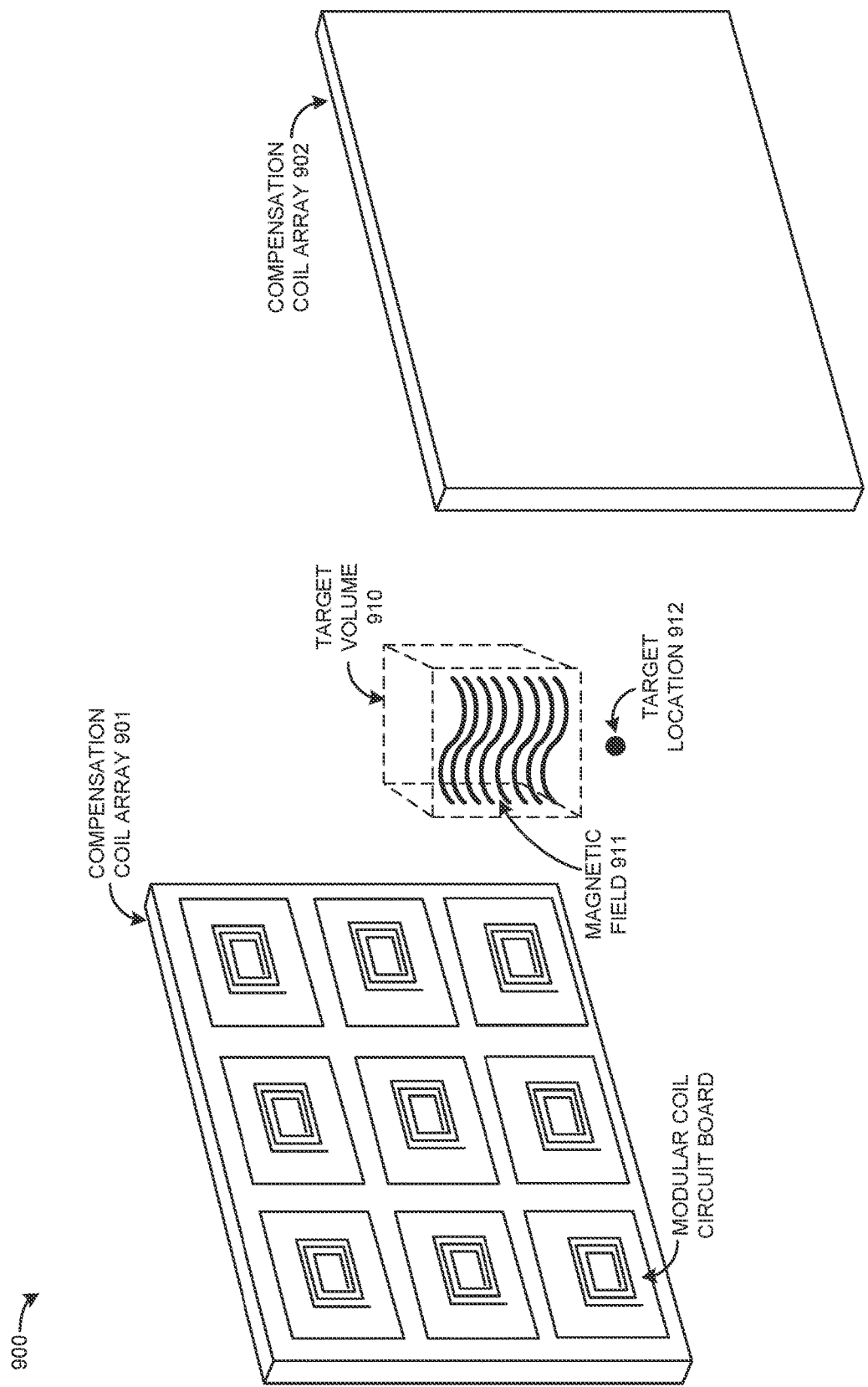
FIG. 9 illustrates an exemplary OPM MEG system to mitigate a background magnetic field.

FIG. 9 illustrates OPM MEG system 900. OPM MEG system 900 comprises an example of OPM MEG system 100, however OPM MEG system 100 may differ. OPM MEG system 900 comprises compensation coil arrays 901-902, target volume 910, magnetic field 911, and target location 912. In this example, compensation coil arrays 901-902 comprise a set of modular coil circuit boards arranged in a grid pattern. Compensation coil arrays 901-902 are positioned facing each other on either side of target location 912. From the perspective illustrated in FIG. 9, compensation coil array 901 is viewed from the front with its constituent modular coil circuit boards visible while compensation coil array 902 is viewed from the rear. The modular coil circuit boards comprise driver circuitry and printed coils. The driver circuitry executes control instructions received from a field controller and transfers current to the printed coils to generate magnetic field 911.

Compensations coil arrays 901-902 generate magnetic field 911 within target volume 910. Target volume 910 is proximate to target location 912 and comprises a region of space with a desired field strength, field gradient, field shape, and/or another field attribute of magnetic field 911. For example, compensation coil arrays 901-902 may generate magnetic field 911 such that magnetic field 911 comprises a homogenous field strength and gradient within target volume 910. Compensation coil arrays 901-902 may generate magnetic field 911 to null background magnetic fields proximate to target location 912 (e.g., within target volume 910). In some examples, compensation coil arrays 901-902 may adjust the amount of current sent to their modular coils circuit boards to move target volume 910 from a first location to a second location. Compensation coil arrays 901-902 may adjust the ratio of current sent to a first one of the modular coil circuit boards and a second one of the modular coil circuit boards based on the distance between arrays 901-902.

Figure 10:
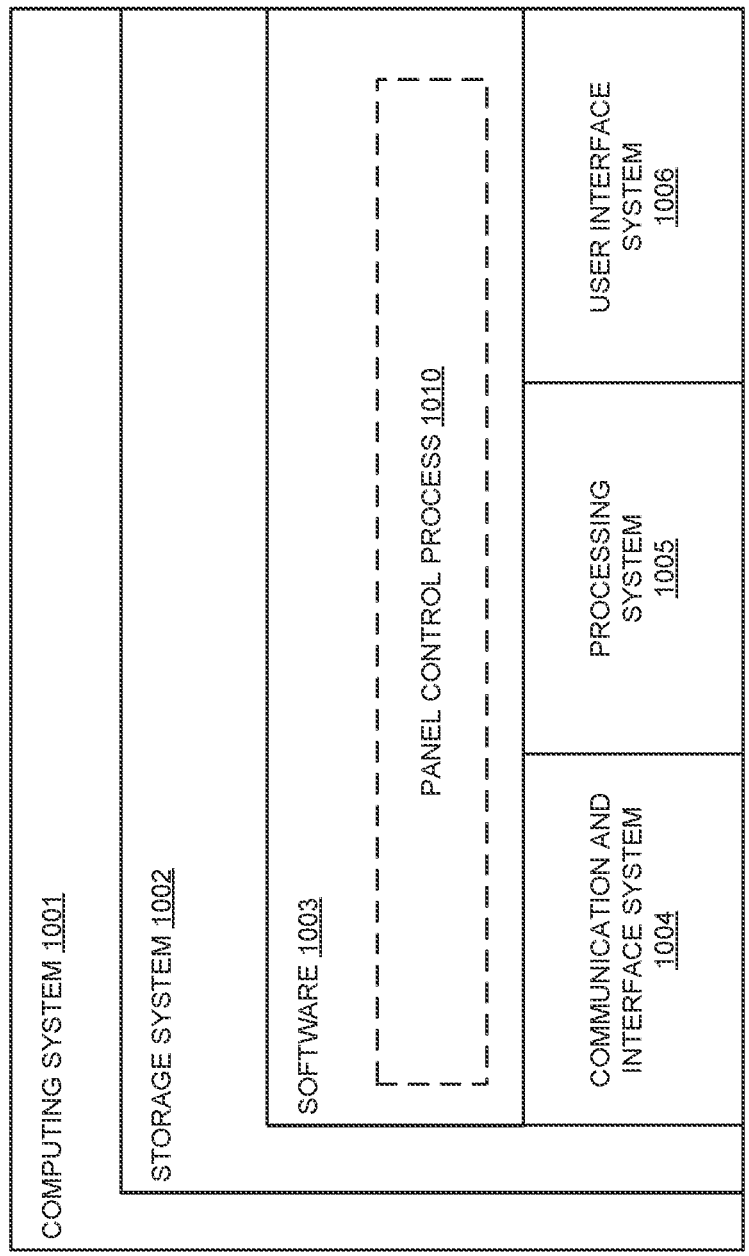
FIG. 10 illustrates an exemplary computing apparatus to operate an OPM MEG system.

FIG. 10 illustrates computing system 1001 according to an implementation of the present technology. Computing system 1001 is representative of any system or collection of systems in which the various processes, programs, services, and scenarios disclosed herein for generating a nulling magnetic field within MEG systems may be implemented.

For example, computing system 1001 may be representative of field controller 101, coil circuit boards 111-119, field controller 801, coil circuit boards 811-817, and/or any other computing device contemplated herein. Examples of computing system 1001 include, but are not limited to, computers, servers, network controllers, routers, web servers, and cloud computing platforms, as well as any other type of physical or virtual server machine, physical or virtual router, container, and any variation or combination thereof. Computing system 1001 may be implemented as a single apparatus, system, or device or may be implemented in a distributed manner as multiple apparatuses, systems, or devices. Computing system 1001 includes, but is not limited to storage system 1002, software 1003, communication interface system 1004, processing system 1005, and user interface system 1006. Processing system 1005 is operatively coupled with storage system 1002, communication interface system 1004, and user interface system 1006.

Processing system 1005 loads and executes software 1003 from storage system 1002. Software 1003 includes and implements panel control process 1010, which is representative of the nulling magnetic field generation processes discussed with respect to the preceding Figures. When executed by processing system 1005, software 1003 directs processing system 1005 to operate as described herein for at least the various processes, operational scenarios, and sequences discussed in the foregoing implementations. Computing system 1001 may optionally include additional devices, features, or functionality not discussed here for purposes of brevity.

Processing system 1005 may comprise a micro-processor and other circuitry that retrieves and executes software 1003 from storage system 1002. Processing system 1005 may be implemented within a single processing device but may also be distributed across multiple processing devices or sub-systems that cooperate in executing program instructions. Examples of processing system 1005 include general purpose CPUs, GPUs, DSPs, ASICs, FPGAs, and logic devices, as well as any other type of processing device, combinations, or variations thereof.

Storage system 1002 may comprise any computer readable storage media that is readable by processing system 1005 and capable of storing software 1003. Storage system 1002 may include volatile and nonvolatile, removable, and non-removable media implemented in any method or technology for storage of information, such as computer readable instructions, data structures, program modules, or other data. Examples of storage media include RAM, read only memory, magnetic disks, optical disks, optical media, flash memory, virtual memory and non-virtual memory, magnetic cassettes, magnetic tape, magnetic disk storage or other magnetic storage devices, or any other suitable storage media. In no case is the computer readable storage media a propagated signal.

In addition to computer readable storage media, in some implementations storage system 1002 may also include computer readable communication media over which at least some of software 1003 may be communicated internally or externally. Storage system 1002 may be implemented as a single storage device but may also be implemented across multiple storage devices or sub-systems co-located or distributed relative to each other. Storage system 1002 may comprise additional elements, such as a controller, capable of communicating with processing system 1005 or possibly other systems.

Software 1003 (panel control process 1010) may be implemented in program instructions and among other functions may, when executed by processing system 1005, direct processing system 1005 to operate as described with respect to the various operational scenarios, sequences, and processes illustrated herein. For example, software 1003 may include program instructions for implementing panel control and null field generation processes as described herein.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 1003 may include additional processes, programs, or components, such as operating system software, virtualization software, or other application software. Software 1003 may also comprise firmware or some other form of machine-readable processing instructions executable by processing system 1005.

In general, software 1003 may, when loaded into processing system 1005 and executed, transform a suitable apparatus, system, or device (of which computing system 1001 is representative) overall from a general-purpose computing system into a special-purpose computing system customized to control printed coil circuit boards to generate a nulling magnetic field. Indeed, encoding software 1003 on storage system 1002 may transform the physical structure of storage system 1002. The specific transformation of the physical structure may depend on various factors in different implementations of this description. Examples of such factors may include, but are not limited to, the technology used to implement the storage media of storage system 1002 and whether the computer-storage media are characterized as primary or secondary storage, as well as other factors.

For example, if the computer readable storage media are implemented as semiconductor-based memory, software 1003 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 1004 may include communication connections and devices that allow for communication with other computing systems (not shown) over communication networks (not shown). Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

Communication between computing system 1001 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses and backplanes, or any other type of network, combination of network, or variation thereof. The aforementioned communication networks and protocols are well known and need not be discussed at length here.

While some examples provided herein are described in the context of computing devices for controlling coil circuit boards and nulling background magnetic fields, it should be understood that the systems and methods described herein are not limited to such embodiments and may apply to a variety of other MEG environments and their associated systems. As will be appreciated by one skilled in the art, aspects of the present invention may be embodied as a system, method, computer program product, and other configurable systems. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number, respectively. The word "or" in reference to a list of two or more items, covers all of the following interpretations of the word: any of the items in the list, all of the items in the list, and any combination of the items in the list.

The phrases "in some embodiments," "according to some embodiments," "in the embodiments shown," "in other embodiments," and the like generally mean the particular feature, structure, or characteristic following the phrase is included in at least one implementation of the present technology and may be included in more than one implementation. In addition, such phrases do not necessarily refer to the same embodiments or different embodiments.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a system claim, other aspects may likewise be embodied as a computer-readable medium claim, or in other forms, such as being embodied in a means-plus-function claim. Any claims intended to be treated under 35 U.S.C. § 112(f) will begin with the words "means for" but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A magnetic field compensation system, the system comprising:
   coil circuit boards arranged in an array that each comprise a printed coil trace pattern;
   coil drivers operatively coupled to the coil circuit boards that correspond to the coil circuit boards on a one-to-one basis;
   a magnetic field controller operatively coupled to the coil drivers;
   the magnetic field controller configured to:
      select current amounts for each of the coil circuit boards to generate a magnetic field with desired field characteristics;
      generate control signaling that indicates the selected current amounts; and transfer the control signaling to corresponding ones of the coil drivers;
the coil drivers configured to receive their respective control signaling and supply the selected current amounts to their corresponding coil circuit boards; and
the coil circuit boards configured to receive the current amounts and generate the magnetic field with the desired field characteristics.

2. The system of claim 1 further comprising:
a magnetic field sensor configured to measure a background magnetic field and report the background magnetic field measurements to the magnetic field controller; and wherein:
the magnetic field controller is configured to select the current amounts for each of the coil circuit boards based on the background magnetic field measurements to generate the magnetic field to null the background magnetic field.

3. The system of claim 2 wherein:
the magnetic field sensor is configured to measure the magnetic field and report the magnetic field measurements to the magnetic field controller; and
the magnetic field controller is configured to:
  adjust the selected current amounts for each of the coil circuit boards based on the magnetic field measurements to adjust the magnetic field;
  generate additional control signaling that indicates the adjusted current amounts; and
  transfer the additional control signaling to the corresponding ones of the coil drivers;
the coil drivers are configured to receive their respective additional control signaling and supply the adjusted current amounts to their corresponding coil circuit boards; and
the coil circuit boards are configured to receive the adjusted current amounts and generate the magnetic field.

4. The system of claim 3 wherein the magnetic field sensor comprises an Optically Pumped Magnetometer (OPM).

5. The system of claim 1 wherein:
the magnetic field controller is configured to:
  select the current amounts for each of the coil circuit boards to generate a volume comprising points of homogeneous magnetic field at a first location; and
  the coil circuit boards are configured to receive the current amounts and generate the volume comprising points of homogeneous magnetic field at the first location.

6. The system of claim 5 wherein:
the magnetic field controller is configured to:
  adjust the selected current amounts for each of the coil circuit boards to move the volume comprising points of homogeneous magnetic field from the first location to a second location;
  generate additional control signaling that indicates the adjusted current amounts; and
  transfer the additional control signaling to the corresponding ones of the coil drivers; and
the coil drivers are configured to receive their respective additional control signaling and supply the adjusted current amounts to their corresponding coil circuit boards; and
the coil circuit boards are configured to receive the adjusted current amounts and move the volume comprising points of homogeneous magnetic field from the first location to the second location.

7. The system of claim 1 wherein:
the coil circuit boards comprise an adhesive configured to mount the coil circuit boards to a surface; and
the coil circuit boards are mounted to surfaces of a magnetically shielded room to form the array.

8. The system of claim 1 wherein the magnetic field controller is configured to:
select current ratios between the coil circuit boards based on a physical arrangement of the coil circuit boards in the array; and
select the current amounts for each of the coil circuit boards based on the current ratios between the coil circuit boards to generate a magnetic field with desired field characteristics.

9. The system of claim 1 further comprising a magnetic field sensor configured to measure the magnetic field and report the magnetic field measurements to the magnetic field controller; and wherein:
the magnetic field controller is configured to determine a spatial characteristic of the magnetic field sensor based on the magnetic field measurements.

10. A method of operating a magnetic field compensation system, the method comprising:
a magnetic field controller selecting current amounts for individual coil circuit boards to generate a magnetic field with desired field characteristics;
the magnetic field controller generating control signaling that indicates the selected current amounts and transferring the control signaling to coil drivers that correspond to the coil circuit boards;
the coil drivers receiving their respective control signaling and supplying the selected current amounts to their corresponding coil circuit boards, wherein the coil drivers correspond to the coil circuit boards on a one-to-one basis; and
the coil circuit boards receiving the current amounts and generating the magnetic field with the desired field characteristics, wherein the coil circuit boards are arranged in an array and each comprise a printed coil trace pattern.

11. The method of claim 10 further comprising:
a magnetic field sensor measuring a background magnetic field and reporting the background magnetic field measurements to the magnetic field controller; and wherein:
the magnetic field controller selecting the current amounts comprises selecting the current amounts for the individual coil circuit boards based on the background magnetic field measurements to generate the magnetic field to null the background magnetic field.

12. The method of claim 11 further comprising:
the magnetic field sensor measuring the magnetic field and reporting the magnetic field measurements to the magnetic field controller;
the magnetic field controller adjusting the selected current amounts for the individual coil circuit boards based on the magnetic field measurements to adjust the magnetic field;
the magnetic field controller generating additional control signaling that indicates the adjusted current amounts and transferring the additional control signaling to the corresponding ones of the coil drivers;
the coil drivers receiving their respective additional control signaling and supplying the adjusted current amounts to their corresponding coil circuit boards; and
the coil circuit boards receiving the adjusted current amounts and generating the magnetic field.

13. The method of claim 12 wherein the magnetic field sensor comprises an Optically Pumped Magnetometer (OPM).

14. The method of claim 10 wherein:
the magnetic field controller selecting the current amounts comprises selecting the current amounts for the individual coil circuit boards to generate a volume comprising points of homogeneous magnetic field at a first location; and
the coil circuit boards receiving the current amounts and generating the magnetic field comprises receiving the current amounts and generating the volume comprising points of homogeneous magnetic field at the first location.

15. The method of claim 14 further comprising:
the magnetic field controller adjusting the selected current amounts for the individual coil circuit boards to move the volume comprising points of homogeneous magnetic field from the first location to a second location;
the magnetic field controller generating additional control signaling that indicates the adjusted current amounts and transferring the additional control signaling to the corresponding ones of the coil drivers;
the coil drivers receiving their respective additional control signaling and supplying the adjusted current amounts to their corresponding coil circuit boards; and
the coil circuit boards receiving the adjusted current amounts and moving the volume comprising points of homogeneous magnetic field from the first location to the second location.

16. The method of claim 10 wherein:
the coil circuit boards comprise an adhesive to mount the coil circuit boards to a surface; and further comprising:
mounting the coil circuit boards to surfaces of a magnetically shielded room to form the array.

17. The method of claim 10 further comprising:
the magnetic field controller selecting current ratios between the coil circuit boards based on a physical arrangement of the coil circuit boards in the array; and wherein:
the magnetic field controller selecting the current amounts for the individual coil circuit boards comprises the magnetic field controller selecting the current amounts for the individual coil circuit boards based on the current ratios between the coil circuit boards to generate the magnetic field with desired field characteristics.

18. The method of claim 10 further comprising:
a magnetic field sensor measuring the magnetic field and reporting the magnetic field measurements to the magnetic field controller; and
the magnetic field controller determining a spatial characteristic of the magnetic field sensor based on the magnetic field measurements.

19. A method of operating a magnetic field controller to generate a magnetic field with desired field characteristics, the method comprising:
receiving information that indicates a physical arrangement of coil circuit boards that form an array;
selecting current ratios for the coil circuit boards based on the physical arrangement of the coil circuit boards in the array;
selecting current amounts for each of the coil circuit boards based on the current ratios between the coil circuit boards to generate the magnetic field with the desired field characteristics;
generating control signaling that indicates the selected current amounts; and
transferring the control signaling to coil drivers that correspond to the coil circuit boards, wherein the coil drivers supply the selected current amounts to their corresponding coil circuit boards and the coil circuit boards generate the magnetic field with the desired field characteristics responsive to receiving the current amounts.

20. The method of claim 19 further comprising:
receiving magnetic field measurements that characterize a background magnetic field; and wherein:
selecting the current amounts for each of the coil circuit boards comprises selecting the current amounts for each of the coil circuit boards based on the current ratios and the background magnetic field measurements to generate the magnetic field that nulls the background magnetic field.

* * * * *